(12) United States Patent
Wang et al.

(10) Patent No.: US 11,254,717 B2
(45) Date of Patent: Feb. 22, 2022

(54) **ANTIMICROBIAL PEPTIDE SPARAMOSIN FROM *SCYLLA PARAMAMOSAIN* AND APPLICATION THEREOF**

(71) Applicant: Xiamen University, Fujian (CN)

(72) Inventors: Kejian Wang, Fujian (CN); Yanchao Chen, Fujian (CN); Fangyi Chen, Fujian (CN); Ying Yang, Fujian (CN); Hui Peng, Fujian (CN); Huiyun Chen, Fujian (CN)

(73) Assignee: Xiamen University, Fujian (CN)

( * ) Notice: Subject to any disclaimer, the term of this patent is extended or adjusted under 35 U.S.C. 154(b) by 0 days.

(21) Appl. No.: 16/944,724

(22) Filed: Jul. 31, 2020

(65) Prior Publication Data

US 2021/0061865 A1    Mar. 4, 2021

Related U.S. Application Data

(63) Continuation of application No. PCT/CN2018/092043, filed on Jun. 20, 2018.

(51) Int. Cl.
| | | |
|---|---|---|
| *A61K 38/16* | (2006.01) | |
| *C07K 14/435* | (2006.01) | |
| *A23K 10/20* | (2016.01) | |
| *A61K 38/00* | (2006.01) | |

(52) U.S. Cl.
CPC ........ *C07K 14/43509* (2013.01); *A23K 10/20* (2016.05); *A61K 38/00* (2013.01)

(58) Field of Classification Search
None
See application file for complete search history.

(56) References Cited

FOREIGN PATENT DOCUMENTS

| CN | 102167736 A | 8/2011 |
| CN | 102304516 A | 1/2012 |
| CN | 103789317 A | 5/2014 |
| CN | 105274134 A | 1/2016 |

OTHER PUBLICATIONS

International Search Report with English Translation, cited in PCT/CN2018/092043 dated Mar. 21, 2019, 8 pages.
Written Opinion cited in PCT/CN2018/122504 dated Mar. 21, 2019, 3 pages.

*Primary Examiner* — Fred H Reynolds
(74) *Attorney, Agent, or Firm* — Cooper Legal Group, LLC

(57) ABSTRACT

Provided is an antimicrobial peptide Sparamosin from *Scylla paramamosain*. The Sparamosin mature peptide and its functional domain Sparamosin$_{26-54}$ were synthesized by solid-phase synthesis with a purity of over 95%. Both Sparamosin and Sparamosin$_{26-54}$ exhibit strong antimicrobial activity. More importantly, Sparamosin$_{26-54}$ has strong antifungal activity and could inhibit the growth of a variety of yeasts and filamentous fungi. Based on the potent antimicrobial activities of Sparamosin and Sparamosin$_{26-54}$, both peptides could be developed as alternatives for conventional antibiotics, antimicrobial agents, feed additives in aquaculture and livestock, preservatives, and mold inhibitors.

7 Claims, 2 Drawing Sheets
Specification includes a Sequence Listing.

ANTIMICROBIAL PEPTIDE SPARAMOSIN FROM *SCYLLA PARAMAMOSAIN* AND APPLICATION THEREOF

RELATED APPLICATIONS

This application is a continuation of and claims priority to PCT/CN2018/092043, filed on Jun. 20, 2018, which is incorporated herein by reference.

REFERENCE TO AN ELECTRONIC SEQUENCE LISTING

The contents of the electronic sequence listing (SequenceListing1.txt; Size: 2,760 bytes; and Date of Creation: Nov. 24, 2021) is herein incorporated by reference.

FIELD OF THE DISCLOSURE

The present disclosure relates to the field of marine biotechnology, in particular to an antimicrobial peptide Sparamosin from *Scylla paramamosain* and applications thereof.

BACKGROUND OF THE DISCLOSURE

Antimicrobial peptides (AMPs), as a kind of small molecules, have been widely found in natural organisms and exhibit broad-spectrum antimicrobial activity. They are considered to be indispensable components of host innate immunity, and play a crucial role in the infection of exogenous pathogens. In addition to their antimicrobial functions, some AMPs have immunomodulatory activity in the body. In 1981, Boman et al. first discovered the AMP cecropin from *Hyalophora cecropia*. Since then, more than 3,000 AMPs have been discovered in plants, insects, marine organisms, amphibians, mammals and microorganisms. Initially, people only found that AMPs had good antibacterial activity. In 1993, the Japanese scientists Iijima et al. isolated a novel AMP from the hemolymph of *Sarcophaga peregrine*, discovering that this AMP is capable of inhibiting the growth of *Candida albicans*, thus named it as "antifungal peptides (AFPs)."

Fungi are a huge group with great diversity, and widely distributed in various ecosystems. At present, more than 200 fungi have been found to be pathogenic. In addition, there are many fungi that can cause mildew of grains (such as cereals and feed), causing tremendous economic losses. Therefore, the research and development of AMPs with antifungal activity has great potential in the development of clinical drugs, preservatives, mold inhibitors and the like. In order to successfully develop and effectively utilize a novel AFP, a clear understanding of its antifungal mechanism is required. There are three main mechanisms: ① AFPs inhibit the synthesis of cell wall components (such as mannoproteins, β-glucan and chitin), leading to the weakening of the cell walls, and ultimately the death of fungal cells; ② AFPs interact with phospholipids in fungal membranes, resulting in the disruption of cell membrane integrity; and ③ AFPs can enter fungal cells and affect many important cellular functions, such as disrupting mitochondrial function, interacting with nucleic acids or inhibiting cell metabolism.

Natural AMPs usually consist of 12-100 amino acids, have good thermal stability and water solubility, have a broad antimicrobial spectrum, and can inhibit the growth of bacteria and fungi. Some AMPs even have a variety of biological activities, such as antiviral, antiparasitic, and anticancer properties. These AMPs have almost no toxic effect on normal mammalian cells and do not easily cause drug resistance of pathogenic microorganisms. In recent years, with the emergence of more and more antibiotic-resistant microorganisms, AMPs have good application prospects in clinical medicine and other fields.

During transportation and long-term storage, feed ingredients are often and easily contaminated by fungi, which can cause harm to animals and even humans. At present, the commonly used mold inhibitors for feed storage and processing are mainly organic acids, organic acid salts, or enzymes, which can inhibit or kill mold. However, the use of organic acids can easily cause corrosion of equipment, feed troughs, etc., and the use of enzyme preparations might be less effective because of low specificity and weak fungicidal activity. The use of AMPs as feed mold inhibitors is a research hotspot in the feed industry. The research, development, and application of AMPs in microbe inhibition and mold prevention in feeds are of great significance for ensuring the quality of feed ingredients, and have highly practical application value in terms of product safety and environmental friendliness.

BRIEF SUMMARY OF THE DISCLOSURE

The technical problem to be solved by the present disclosure is to provide novel, safe and efficient AMPs Sparamosin and Sparamosin$_{26-54}$ from *S. paramamosain* and applications thereof.

The first object of the present disclosure is to provide a process for the preparation of Sparamosin and Sparamosin$_{26-54}$.

The second object of the present disclosure is to provide an application of Sparamosin and Sparamosin$_{26-54}$ in the preparation of antimicrobial agents.

The third object of the present disclosure is to provide an application of Sparamosin and Sparamosin$_{26-54}$ in the preparation of preservatives and mold inhibitors.

An open reading frame sequence of Sparamosin is SEQ ID NO 01, and a sequence of SEQ ID NO 01 is as follows:

ATGGCGCGCCACGTGCTCCCGCTGGTGTTGCTACTTGTGGCTCTTGTGGT

GCGACTCATTTTGTCTGCACCTGTCCCTGATCCAGACTCTGAACAGAGCA

ATATATCTGAAGTGCTAAAGGTGCAACATTCCATCTTCAGCGGCCTGGGC

CCCAACCCGTGCCGCAAGAAATGCTACAAAAGGGATTTCTTGGGTCGATG

TCGCCTGAATTTCACATGTATGTTTGGATGA.

An amino acid sequence of Sparamosin is SEQ ID NO 02, and a sequence of SEQ ID NO 02 is as follows:

Met-Ala-Arg-His-Val-Leu-Pro-Leu-Val-Leu-Leu-Leu-

Val-Ala-Leu-Val-Val-Arg-Leu-Ile-Leu-Ser-Ala-Pro-

Val-Pro-Asp-Pro-Asp-Ser-Glu-Gln-Ser-Asn-Ile-Ser-

Glu-Val-Leu-Lys-Val-Gln-His-Ser-Ile-Phe-Ser-Gly-

Leu-Gly-Pro-Asn-Pro-Cys-Arg-Lys-Lys-Cys-Tyr-Lys-

Arg-Asp-Phe-Leu-Gly-Arg-Cys-Arg-Leu-Asn-Phe-Thr-

Cys-Met-Phe-Gly, where SEQ ID NO 11 represents signal peptide, and a sequence of SEQ ID NO 11 is Met-Ala-Arg-His-Val-Leu-Pro-Leu-Val-Leu-Leu-Leu-Val-Ala-Leu-Val-Val-Arg-Leu-Ile-Leu-Ser.

The amino acid sequence of Sparamosin is 76 residues in length and consists of a 22-amino acid signal peptide. The putative signal peptide cleavage site predicted by the SignalP-4.1 Server (http://www.cbs.dtu.dk/services/SignalP/) is between $Ser^{22}$ and $Ala^{23}$. The Sparamosin mature peptide consists of 54 amino acids with the molecular formula $C_{266}H_{419}N_{77}O_{77}S_5$. The molecular weight is 6.09 kDa. The grand average of hydropathicity is −0.476, indicating that Sparamosin mature peptide has high solubility in water. The theoretical pI is 8.87, with eight positively charged residues and five negatively charged residues, corresponding to the cationic peptide.

The amino acid sequence of $Sparamosin_{26-54}$ is SEQ ID NO 03, and a sequence of SEQ ID NO 03 is as follows:

Gly-Leu-Gly-Pro-Asn-Pro-Cys-Arg-Lys-Lys-Cys-Tyr-

Lys-Arg-Asp-Phe-Leu-Gly-Arg-Cys-Arg-Leu-Asn-Phe-

Thr-Cys-Met-Phe-Gly.

$Sparamosin_{26-54}$ is the functional domain of Sparamosin mature peptide, which is formed from the 26th (glycine) to 54th (glycine) amino acid residue of the mature peptide. $Sparamosin_{26-54}$ is composed of 29 amino acids and its molecular formula is $C_{147}H_{234}N_{46}O_{36}S_5$. The molecular weight is 3.38 kDa. The grand average of hydropathicity is −0.528, indicating that $Sparamosin_{26-54}$ has high solubility in water. The theoretical pI is 9.79, with seven positively charged residues and one negatively charged residue, corresponding to the cationic peptide.

The Sparamosin mature peptide and its functional domain $Sparamosin_{26-54}$ were synthesized by solid-phase synthesis with a purity of over 95%.

The AMPs Sparamosin and $Sparamosin_{26-54}$ exhibited significant antimicrobial activity against Gram-positive bacteria, Gram-negative bacteria and fungi. Compared with Sparamosin, $Sparamosin_{26-54}$ has a stronger antimicrobial activity—the minimum inhibitory concentration (MIC) value against various Gram-positive bacteria and Gram-negative bacteria is 3-12 μM, and the MIC value against various molds is 6-24 μM. In addition, $Sparamosin_{26-54}$ has no cytotoxic effect on normal cultured mammalian cells, such as normal cultured mouse hepatocytes and normal cultured human hepatocytes. Compared with many known marine animal AMPs, $Sparamosin_{26-54}$ has better antimicrobial activity, broader antimicrobial spectrum and a faster sterilization rate. Therefore, $Sparamosin_{26-54}$ has great application value, and also has good application in the development and preparation of antimicrobial agents.

According to the amino acid sequence of the marine animal S. paramamosain, the present disclosure provides two synthetic AMPs with broad-spectrum antimicrobial activity. The AMPs are derived from crustacean, which can be applied to aquaculture as a feed additive, and can also be developed as alternatives for conventional antibiotics, antimicrobial agents, preservatives, and mold inhibitors. Therefore, the present disclosure has wide application prospects.

In the present disclosure, the transcriptome database of S. paramamosain was screened, and a new AMP gene Sparamosin was obtained. The Sparamosin mature peptide and its functional domain $Sparamosin_{26-54}$ were synthesized by solid-phase synthesis with a purity over 95%. It has been found that both Sparamosin and $Sparamosin_{26-54}$ have strong antibacterial activity, while $Sparamosin_{26-54}$ also has strong antifungal activity. The present disclosure is the first report of the endogenous AMPs Sparamosin and $Sparamosin_{26-54}$ from S. paramamosain.

BRIEF DESCRIPTION OF THE DRAWINGS

In FIG. 2, the X-axis is time (min), and the Y-axis is the kill index (%).

In FIG. 3, the X-axis is time (h), and the Y-axis is the $OD_{600}$ value.

In FIG. 4, the X-axis is the concentration of $Sparamosin_{26-54}$ (μg/mL), and the Y-axis is the cell proliferation rate (%).

DETAILED DESCRIPTION OF THE EMBODIMENTS

Figure 1:
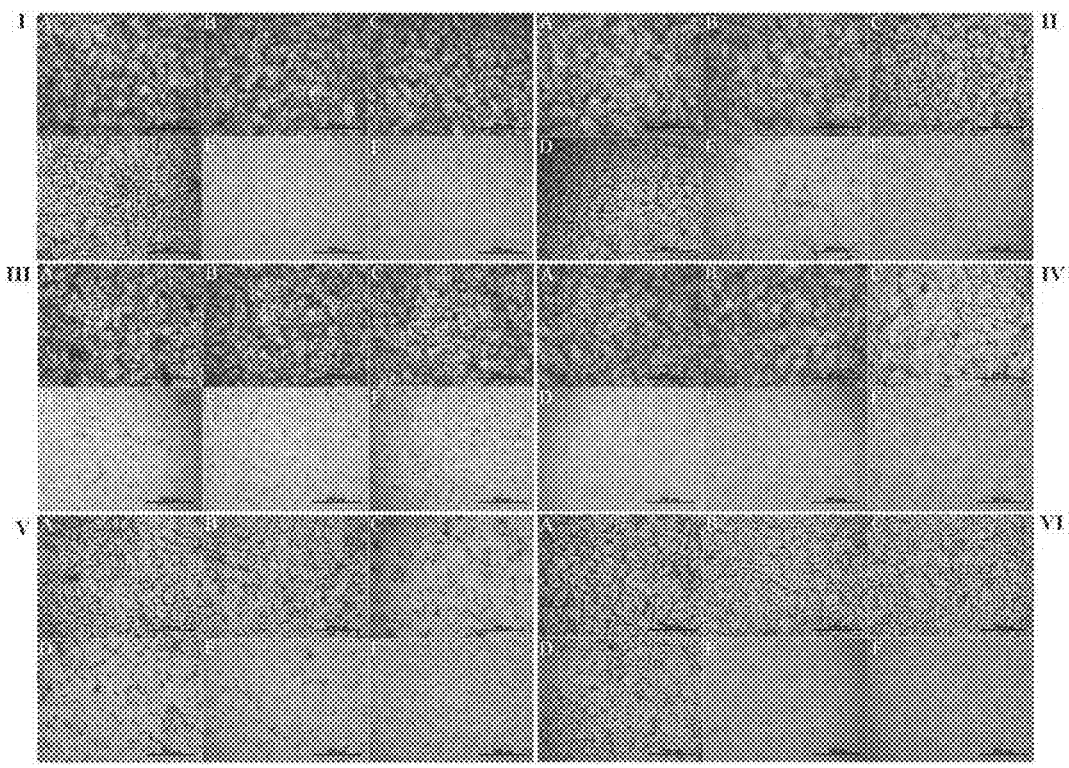
FIG. 1 shows the inhibition of $Sparamosin_{26-54}$ on spore germination of Aspergillus niger, Neurospora crassa, Fusarium graminearum, Fusarium oxysporum, Aspergillus ochraceus and Aspergillus fumigatus. (I): A. niger, (II): N. crassa, (III): F. graminearum, (IV): F. oxysporum, (V): A. ochraceus, (VI): A. fumigatus. The final concentration of $Sparamosin_{26-54}$ is as follows: A: 0 μM; B: 3 μM; C: 6 μM; D: 12 μM; E: 24 μM; and F: 48 μM.

The following embodiments can enable those skilled in the art to fully understand the present disclosure, and the present disclosure is not limited to the embodiments below.

Embodiment 1: Preparation of Sparamosin and $Sparamosin_{26-54}$

The ORF sequence of Sparamosin is SEQ ID NO 01, and a sequence of SEQ ID NO 01 is as follows:

ATGGCGCGCCACGTGCTCCCGCTGGTGTTGCTACTTGTGGCTCTTGTGGT

GCGACTCATTTTGTCTGCACCTGTCCCTGATCCAGACTCTGAACAGAGCA

ATATATCTGAAGTGCTAAAGGTGCAACATTCCATCTTCAGCGGCCTGGGC

CCCAACCCGTGCCGCAAGAAATGCTACAAAAGGGATTTCTTGGGTCGATG

TCGCCTGAATTTCACATGTATGTTTGGATGA

The full length cDNA sequence of Sparamosin was obtained using 5' RACE and 3' RACE PCR and sequence splicing. The ORF of Sparamosin is 231 bp (containing the termination codon TGA), with the gene accession number in GenBank as MH423837.

Gene-specific primers were designed according to the cDNA sequence of Sparamosin in the sequencing results of transcriptome (Table 1).

TABLE 1

The sequence amplification primers of Sparamosin

| Primer Name | Sequence 5'-3' |
|---|---|
| Sparamosin 5' 1 | CCCAGGCCGCTGAAGATGGAATGTT |
| Sparamosin 5' 2 | TGAGTCGCACCACAAGAGCCACA |

TABLE 1-continued

The sequence amplification primers of Sparamosin

| Primer Name | Sequence 5'-3' |
|---|---|
| Sparamosin 3' 1 | TGTGGCTCTTGTGGTGCGACTCA |
| Sparamosin 3' 2 | TGTCTGCACCTGTCCCTGATCCA |
| Long Primer | CTAATACGACTCACTATAGGGCAAGCAGTGG TATCAACGCAGAGT |
| Short Primer | CTAATACGACTCACTATAGGGC |
| UPM | The mixing ratio is as follows: Long Primer:Short Primer = 1:4 |
| NUP | AAGCAGTGGTATCAACGCAGAGT |

Sparamosin 5' untranslated region (UTR) was amplified by 5' RACE

First Round of PCR Reaction

The cDNA we previously prepared in this laboratory was used as a template for PCR, and the PCR reaction system is as follows:

| Template | 1.25 µL |
|---|---|
| 10 × LA PCR Buffer II (Mg$^{2+}$ plus) | 2.5 µL |
| dNTP Mixture (2.5 mM each) | 4 µL |
| UPM | 2.5 µL |
| Sparamosin 5'1 | 1 µL |
| LA Taq (5 U/µL) | 0.25 µL |
| Milli-Q water | 13.5 µL |
| Total reaction volume | 25 µL |

The PCR reaction was carried out after mixing evenly and the reaction procedure was as follows:
(1) pre-denaturation at 95° C. for 5 min;
(2) denaturation at 95° C. for 30 s, annealing at 60° C. for 30 s, extension at 72° C. for 2 min, repeating for 30 cycles;
(3) extension at 72° C. for 10 min; and
(4) termination at 16° C.

Second Round of PCR Reaction

The first-round of PCR amplification products was diluted 50 times with Milli-Q water, and then used as a template for the second round PCR reaction. The PCR reaction system is as follows:

| Template | 2.5 µL |
|---|---|
| 10 × LA PCR Buffer II (Mg$^{2+}$ plus) | 5 µL |
| dNTP Mixture (2.5 mM each) | 8 µL |
| NUP | 2 µL |
| Sparamosin 5'2 | 2 µL |
| LA Taq (5 U/µL) | 0.5 µL |
| Milli-Q water | 30 µL |
| Total reaction volume | 50 µL |

The PCR reaction was carried out after mixing evenly and the reaction procedure was as follows:
(1) pre-denaturation at 95° C. for 5 min;
(2) denaturation at 95° C. for 30 s, annealing at 60° C. for 30 s, extension at 72° C. for 2 min, repeating for 30 cycles;
(3) extension at 72° C. for 10 min; and
(4) termination at 16° C.

Sparamosin 3' UTR was amplified by 3' RACE

The amplification method of Sparamosin 3' UTR is similar to 5' UTR amplification.

The amino acid sequence of Sparamosin is SEQ ID NO 02, and a sequence of SEQ ID NO 02 is as follows:

Met-Ala-Arg-His-Val-Leu-Pro-Leu-Val-Leu-Leu-
Val-Ala-Leu-Val-Val-Arg-Leu-Ile-Leu-Ser-Ala-Pro-
Val-Pro-Asp-Pro-Asp-Ser-Glu-Gln-Ser-Asn-Ile-Ser-
Glu-Val-Leu-Lys-Val-Gln-His-Ser-Ile-Phe-Ser-Gly-
Leu-Gly-Pro-Asn-Pro-Cys-Arg-Lys-Lys-Cys-Tyr-Lys-
Arg-Asp-Phe-Leu-Gly-Arg-Cys-Arg-Leu-Asn-Phe-Thr-
Cys-Met-Phe-Gly, where SEQ ID NO 11 represents signal peptide, and a sequence of SEQ ID NO 11 is Met-Ala-Arg-His-Val-Leu-Pro-Leu-Val-Leu-Leu-Leu-Val-Ala-Leu-Val-Val-Arg-Leu-Ile-Leu-Ser.

The amino acid sequence of Sparamosin is 76 residues in length and consists of a 22-amino acid signal peptide. The putative signal peptide cleavage site predicted by the SignalP-4.1 Server (http://www.cbs.dtu.dk/services/SignalP/) is between Ser$^{22}$ and Ala$^{23}$. The Sparamosin mature peptide consists of 54 amino acids with the molecular formula $C_{266}H_{419}N_{77}O_{77}S_5$. The molecular weight is 6.09 kDa. The grand average of hydropathicity is −0.476, indicating that Sparamosin mature peptide has high solubility in water. The theoretical pI is 8.87, with eight positively charged residues and five negatively charged residues, corresponding to the cationic peptide.

The amino acid sequence of Sparamosin$_{26-54}$ is SEQ ID NO 03, and a sequence of SEQ ID NO 03 is as follows:

Gly-Leu-Gly-Pro-Asn-Pro-Cys-Arg-Lys-Lys-Cys-Tyr-
Lys-Arg-Asp-Phe-Leu-Gly-Arg-Cys-Arg-Leu-Asn-Phe-
Thr-Cys-Met-Phe-Gly.

Sparamosin$_{26-54}$ is the functional domain of Sparamosin mature peptide, which is formed from the 26th (glycine) to 54th (glycine) amino acid residue of the mature peptide. Sparamosin$_{26-54}$ is composed of 29 amino acids and its molecular formula is $C_{147}H_{234}N_{46}O_{36}S_5$. The molecular weight is 3.38 kDa. The grand average of hydropathicity is −0.528, indicating that Sparamosin$_{26-54}$ has high solubility in water. The theoretical pI is 9.79, with seven positively charged residues and one negatively charged residue, corresponding to the cationic peptide.

The Sparamosin and Sparamosin$_{26-54}$ were synthesized by solid-phase synthesis with a purity of over 95%. In this embodiment, these two peptides were commercially synthesized by Jinken biochemical reagent (Wuhan, China) and Genscript (Nanjing, China).

Embodiment 2: The Determination of the MIC and Minimum Bactericidal Concentration (MBC) of Sparamosin and Sparamosin$_{26-54}$ The strains involved in this embodiment include: *S. aureus, Corynebacterium glutamicum, Bacillus cereus, Pseudomonas fluorescens, Pseudomonas aeruginosa, Escherichia coli, C. neoformans, C. albicans, Pichia pastoris* GS115, *A. niger, Aspergillus flavus, F. graminearum, F. oxysporum, A. ochraceus, A. fumigatus*, and *N. crasa*. *P. pastoris* GS115 was purchased from the company Invitrogen, and all other strains were purchased from China General Microbiological Culture Collection Center (CGMCC), which were stored in this lab.

① S. aureus, C. glutamicum, B. cereus, P. fluorescens, P. aeruginosa, E. coli were inoculated on nutrient broth (NB) agar and cultured for 1-2 days. C. neoformans, C. albicans, P. pastoris GS115 were inoculated on yeast extract peptone dextrose (YPD) agar and cultured at 28° C. for 1-3 days. The spores of A. niger, A. flavus, F. graminearum, F. oxysporum, A. ochraceus, A. fumigatus, N. crasa were inoculated on potato dextrose agar (PDA) and cultured at 28° C. for 1-7 days.

② Strains were then inoculated on the corresponding solid culture medium: the bacteria was further cultured for 1-2 days; the yeasts were further cultured for 1-3 days; and the molds were further cultured for 1-7 days. Bacteria and yeast were washed away from the solid culture medium with 10 mM sodium phosphate buffer (pH=7.4). A mixed solution of Mueller-Hinton (MH) medium and sodium phosphate buffer solution was used to dilute the bacteria, and a mixed solution of YPD medium and sodium phosphate buffer solution was used to dilute the yeasts, so that the final concentration of the bacteria or yeasts became $3.3 \times 10^4$ cfu/mL. The mold spores were washed away from the solid culture medium with 10 mM sodium phosphate buffer and diluted in a mixed solution of potato dextrose broth and sodium phosphate buffer. The concentration of spores was determined using a hemocytometer under an optical microscope and adjusted to $5 \times 10^4$ spores/mL.

③ Sparamosin and Sparamosin$_{26-54}$ were diluted to 3, 6, 12, 24, 48 and 96 μM with sterilized Milli-Q water. The peptide solutions should be filter-sterilized using a 0.22 μm pore size filter.

④ Each test was set up with a sterile control, a negative control group and an experimental group in sterile 96-well microtiter plates. All measurements were repeated three times.
a. sterile control: 50 μL of peptide solution with 50 μL of culture medium, b. negative control: 50 μL of sterilized Milli-Q water with 50 μL of microbial suspension, and c. experimental group: 50 μL of peptide solution with 50 μL of microbial suspension.

The cultures were grown at 28° C. or 37° C. for 1-2 days. The test isolates without visible growth were then placed on an appropriate medium and incubated at 28° C. or 37° C. for 1-2 days.

The results of MIC and MBC of Sparamosin are shown in Table 2.

TABLE 2

MIC and MBC of synthetic Sparamosin

| Microorganism | CGMCC NO. | MIC | MBC |
|---|---|---|---|
| Gram-positive bacteria | | | |
| Bacillus cereus | 1.3760 | 24-48 | >48 |
| Staphylococcus aureus | 1.2465 | 12-24 | 48 |
| Gram-negative bacteria | | | |
| Pseudomonas fluorescens | 1.3202 | 12-24 | 24 |
| Escherichia coli | 1.2389 | 12-24 | 24 |
| Fungi | | | |
| Cryptococcus neoformans | 2.1563 | >48 | >48 |
| Pichia pastoris (GS115) | Invitrogen | 6-12 | 24 |

The results of MIC and MBC of Sparamosin$_{26-54}$ are shown in Table 3.

TABLE 3

MIC and MBC of synthetic Sparamosin$_{26-54}$

| Microorganism | CGMCC NO. | MIC | MBC |
|---|---|---|---|
| Gram-positive bacteria | | | |
| Staphylococcus aureus | 1.2465 | 3-6 | 12 |
| Corynebacterium glutamicum | 1.1886 | 1.5-3 | 6 |
| Bacillus cereus | 1.3760 | 6-12 | 24 |
| Gram-negative bacteria | | | |
| Pseudomonas fluorescens | 1.3202 | 3-6 | 6 |
| Pseudomonas aeruginosa | 1.2421 | 6-12 | 12 |
| Escherichia coli | 1.2389 | 6-12 | 12 |
| Fungi | | | |
| Cryptococcus neoformans | 2.1563 | 1.5-3 | 12 |
| Pichia pastoris (GS115) | Invitrogen | 1.5-3 | 3 |
| Candida albicans | 2.2411 | >48 | >48 |
| Aspergillus niger | 3.316 | 6-12 | 24 |
| Aspergillus flavus | 3.441 | >48 | >48 |
| Fusarium graminearum | 3.4521 | 6-12 | 12 |
| Fusarium oxysporum | 3.6785 | 6-12 | 12 |
| Aspergillus ochraceus | 3.5830 | 3-6 | 48 |
| Aspergillus fumigatus | 3.5835 | 12-24 | 24 |
| Neurospora crasa | 3.1604 | 12-24 | 48 |

MIC: minimum inhibitory concentration (μM), expressed a-b. a: The highest peptide concentration that induce visible growth of microorganisms. b: The lowest peptide concentration that does not induce visible growth of microorganisms;
MBC: minimum bactericidal concentration (μM), the lowest peptide concentration killed more than 99.9% of bacteria;

Embodiment 3: Anti-Mold Properties of Sparamosin$_{26-54}$

① The spores of A. niger, N. crasa, F. graminearum, F. oxysporum, A. ochraceus, and A. fumigatus were inoculated on PDA plates and cultured at 28° C. for 1-7 days.

② Molds were then inoculated on the PDA plates and cultured at 28° C. for 1-7 days. The mold spores were washed away from solid culture medium with 10 mM sodium phosphate buffer and diluted in a mixed solution of potato dextrose broth and sodium phosphate buffer. The concentration of spores was determined using a hemocytometer under an optical microscope and adjusted to $5 \times 10^4$ spores/mL.

③ Sparamosin and Sparamosin$_{26-54}$ were diluted to 3, 6, 12, 24, 48 and 96 μM with sterilized Milli-Q water. The peptide solutions should be filter-sterilized using a 0.22-μm pore size filter.

④ Each test was set up with a negative control group and an experimental group in sterile 96-well microtiter plates. All measurements were repeated three times.
a. negative control: 50 μL of sterilized Milli-Q water with 50 μL of spore suspension, and
b. experimental group: 50 μL of peptide solution with 50 μL of spore suspension.

Cultures were grown at 28° C. for 24 hours. Spores germination were observed under an optical microscope (see FIG. 1).

Embodiment 4: Time-Kill Curve of Sparamosin$_{26-54}$

The time-killing kinetic curve of Sparamosin$_{26-54}$ was performed using S. aureus and C. neoformans. The final concentration of Sparamosin$_{26-54}$ was adjusted to 1×MBC (S. aureus: 12 μM, C. neoformans: 12 μM). This procedure is similar to the antimicrobial assay described in Embodiment 2.

At 10, 15, 30, 60, 180 and 360 minutes of incubation, a mixed solution of 6 μL of *S. aureus* and synthetic Sparamosin$_{26-54}$ from each test was diluted into 600 μL of 10 mM sodium phosphate buffer. After mixing evenly, 40 μL of the solution was taken out and plated on NB agar. The number of *S. aureus* monoclonal was recorded, and the percentage of CFU was calculated after incubation at 37° C. for 1-2 days.

At 15, 30, 60, 120, 240, 360 and 480 minutes of incubation, a mixed solution of 40 μL of *C. neoformans* and synthetic Sparamosin$_{26-54}$ was taken from each test and plated on YPD agar. The number of *C. neoformans* monoclonal was recorded and the percentage of CFU was calculated after incubation at 28° C. for 1-2 days.

Figure 2:
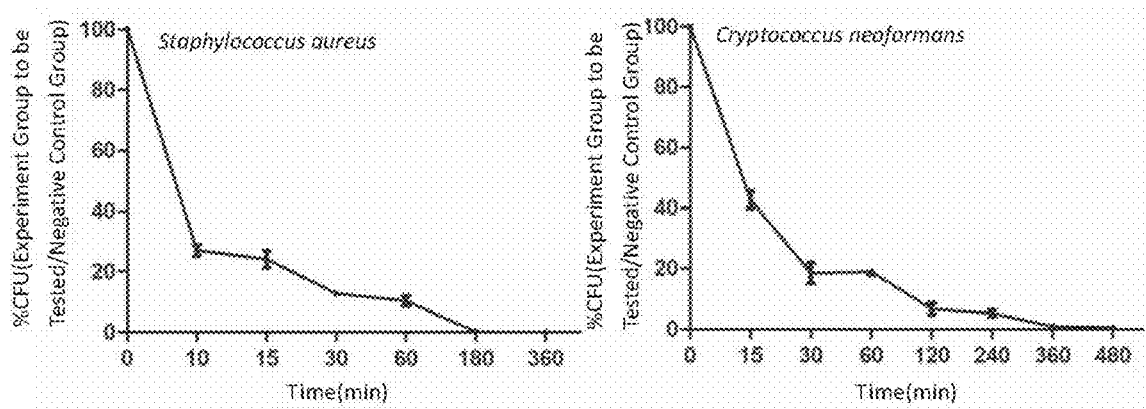
FIG. 2 is a time-kill curve of $Sparamosin_{26-54}$ killing Staphylococcus aureus and Cryptococcus neoformans.

The percentage of CFU is defined relative to the CFU obtained in the control (see FIG. 2).

Embodiment 5: The Thermal Stability of Sparamosin$_{26-54}$ Against *S. aureus* and *C. neoformans*

Figure 3:
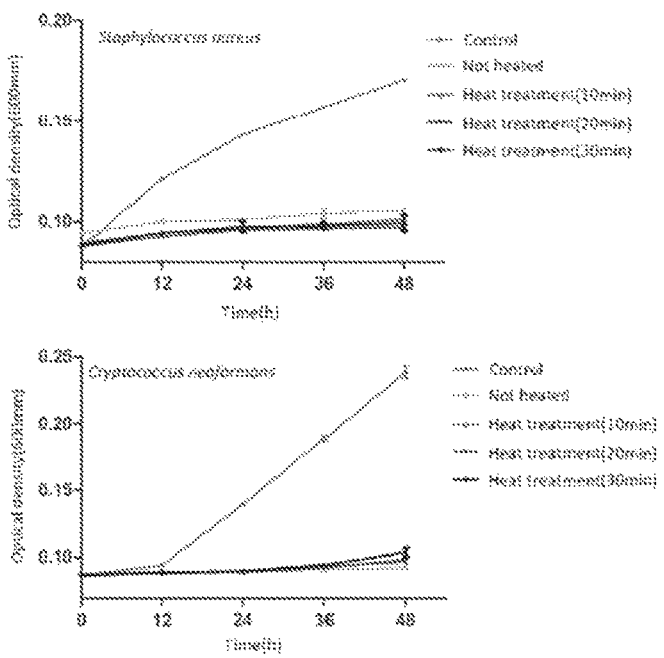
FIG. 3 shows the thermal stability of $Sparamosin_{26-54}$ against S. aureus and C. neoformans.

The thermal stability of Sparamosin$_{26-54}$ was performed using *S. aureus* and *C. neoformans*. The procedure is similar to the antimicrobial assay described in Embodiment 2. The final concentration of Sparamosin$_{26-54}$ was adjusted to 1×MBC (*S. aureus:* 12 μM, *C. neoformans:* 12 μM). The Sparamosin$_{26-54}$ solution was heated at 100° C. for 10, 20 and 30 minutes. After cooling, Sparamosin$_{26-54}$ or sterile Milli-Q water was incubated with microorganisms. Growth inhibition was evaluated by measuring absorbance value of the solution at 600 nm at 0, 12, 24, 36 and 48 h (see FIG. 3).

Embodiment 6 Determination of Cytotoxicity Effect of Synthetic Sparamosin$_{26-54}$ The cytotoxicity effect of synthetic Sparamosin$_{26-54}$ was evaluated using normal mouse liver cell line (AML12 cell line) and normal human liver cell line (L02 cell line).

① AML12 or L02 cells were harvested, and the cell concentration was adjusted to $10^5$ cells/mL.

② 100 μL of AML12 or L02 cells were seeded in 96-wells and incubated at 37° C.

③ Cells were treated with different concentrations of Sparamosin$_{26-54}$ (0, 0.1, 1, 10, 100 μg/mL) for 24 h at 37° C.

Figure 4:
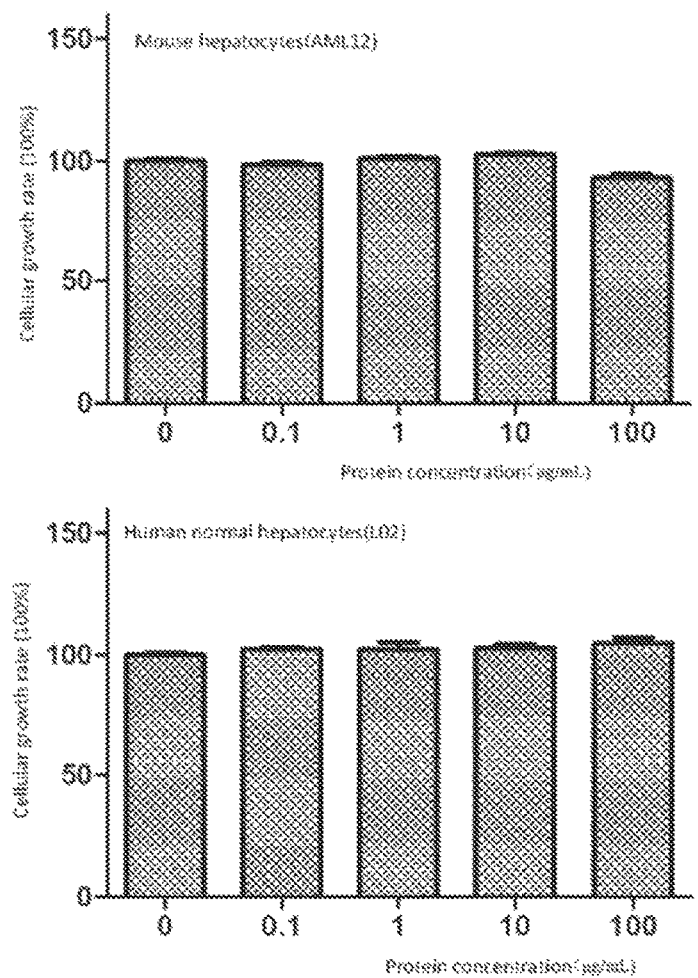
FIG. 4 shows the cytotoxicity test of $Sparamosin_{26-54}$ determined by MTS-PMS-assay.

④ Cells were treated with 20 μL of MTS-PMS reagent for another 2 hours, and then the absorbance value of each well was measured at 492 nm (see FIG. 4).

What is claimed is:

1. A functional domain Sparamosin$_{26\text{-}54}$, wherein the amino acid sequence is SEQ ID NO 03.

2. The functional domain Sparamosin$_{26\text{-}54}$ according to claim 1, wherein the functional domain Sparamosin$_{26\text{-}54}$ has antifungal activity.

3. The functional domain Sparamosin$_{26\text{-}54}$ according to claim 1, wherein the functional domain Sparamosin$_{26\text{-}54}$ has antimicrobial activity.

4. A method for preparing the functional domain Sparamosin$_{26\text{-}54}$ according to claim 1, comprising:
synthesizing the functional domain Sparamosin$_{26\text{-}54}$ by a solid-phase synthesis.

5. A method, comprising:
diluting the functional domain Sparamosin$_{26\text{-}54}$ according to claim 1 to prepare antimicrobial agents.

6. A method, comprising:
diluting the functional domain Sparamosin$_{26\text{-}54}$ according to claim 1 to prepare feed additives.

7. A method, comprising:
diluting the functional domain Sparamosin$_{26\text{-}54}$ according to claim 1 to prepare preservatives and mold inhibitors.

* * * * *

SEQUENCE LISTING

```
<160> NUMBER OF SEQ ID NOS: 11

<210> SEQ ID NO 1
<211> LENGTH: 231
<212> TYPE: DNA
<213> ORGANISM: Artificial Sequence
<220> FEATURE:
<223> OTHER INFORMATION: Synthesized

<400> SEQUENCE: 1
atggcgcgcc acgtgctccc gctggtgttg ctacttgtgg ctcttgtggt gcgactcatt     60
ttgtctgcac ctgtccctga tccagactct gaacagagca atatatctga agtgctaaag    120
gtgcaacatt ccatcttcag cggcctgggc cccaacccgt gccgcaagaa atgctacaaa    180
agggatttct tgggtcgatg tcgcctgaat ttcacatgta tgtttggatg a              231

<210> SEQ ID NO 2
<211> LENGTH: 76
<212> TYPE: PRT
<213> ORGANISM: Artificial Sequence
<220> FEATURE:
<223> OTHER INFORMATION: Synthesized

<400> SEQUENCE: 2

Met Ala Arg His Val Leu Pro Leu Val Leu Leu Leu Val Ala Leu Val
1               5                   10                  15

Val Arg Leu Ile Leu Ser Ala Pro Val Pro Asp Pro Asp Ser Glu Gln
            20                  25                  30

Ser Asn Ile Ser Glu Val Leu Lys Val Gln His Ser Ile Phe Ser Gly
        35                  40                  45

Leu Gly Pro Asn Pro Cys Arg Lys Lys Cys Tyr Lys Arg Asp Phe Leu
    50                  55                  60

Gly Arg Cys Arg Leu Asn Phe Thr Cys Met Phe Gly
65                  70                  75

<210> SEQ ID NO 3
<211> LENGTH: 29
<212> TYPE: PRT
```

<213> ORGANISM: Artificial Sequence
<220> FEATURE:
<223> OTHER INFORMATION: Synthesized

<400> SEQUENCE: 3

```
Gly Leu Gly Pro Asn Pro Cys Arg Lys Lys Cys Tyr Lys Arg Asp Phe
1               5                   10                  15

Leu Gly Arg Cys Arg Leu Asn Phe Thr Cys Met Phe Gly
            20                  25
```

<210> SEQ ID NO 4
<211> LENGTH: 25
<212> TYPE: DNA
<213> ORGANISM: Artificial Sequence
<220> FEATURE:
<223> OTHER INFORMATION: Synthesized

<400> SEQUENCE: 4
cccaggccgc tgaagatgga atgtt                                         25

<210> SEQ ID NO 5
<211> LENGTH: 23
<212> TYPE: DNA
<213> ORGANISM: Artificial Sequence
<220> FEATURE:
<223> OTHER INFORMATION: Synthesized

<400> SEQUENCE: 5
tgagtcgcac cacaagagcc aca                                           23

<210> SEQ ID NO 6
<211> LENGTH: 23
<212> TYPE: DNA
<213> ORGANISM: Artificial Sequence
<220> FEATURE:
<223> OTHER INFORMATION: Synthesized

<400> SEQUENCE: 6
tgtggctctt gtggtgcgac tca                                           23

<210> SEQ ID NO 7
<211> LENGTH: 23
<212> TYPE: DNA
<213> ORGANISM: Artificial Sequence
<220> FEATURE:
<223> OTHER INFORMATION: Synthesized

<400> SEQUENCE: 7
tgtctgcacc tgtccctgat cca                                           23

<210> SEQ ID NO 8
<211> LENGTH: 45
<212> TYPE: DNA
<213> ORGANISM: Artificial Sequence
<220> FEATURE:
<223> OTHER INFORMATION: Synthesized

<400> SEQUENCE: 8
ctaatacgac tcactatagg gcaagcagtg gtatcaacgc agagt                   45

<210> SEQ ID NO 9
<211> LENGTH: 22
<212> TYPE: DNA
<213> ORGANISM: Artificial Sequence
<220> FEATURE:
<223> OTHER INFORMATION: Synthesized

```
<400> SEQUENCE: 9
ctaatacgac tcactatagg gc                                           22

<210> SEQ ID NO 10
<211> LENGTH: 23
<212> TYPE: DNA
<213> ORGANISM: Artificial Sequence
<220> FEATURE:
<223> OTHER INFORMATION: Synthesized

<400> SEQUENCE: 10
aagcagtggt atcaacgcag agt                                          23

<210> SEQ ID NO 11
<211> LENGTH: 22
<212> TYPE: PRT
<213> ORGANISM: Artificial Sequence
<220> FEATURE:
<223> OTHER INFORMATION: Synthesized

<400> SEQUENCE: 11

Met Ala Arg His Val Leu Pro Leu Val Leu Leu Val Ala Leu Val
1               5                   10                  15

Val Arg Leu Ile Leu Ser
            20
```